US008236356B2

(12) United States Patent
Suppmann et al.

(10) Patent No.: US 8,236,356 B2
(45) Date of Patent: Aug. 7, 2012

(54) **GROWTH MEDIUM FOR *CLOSTRIDIUM HISTOLYTICUM***

(75) Inventors: Bernhard Suppmann, Weilheim (DE); Werner Hoelke, Penzberg (DE); Artur Hoffmann, Wolfratshausen (DE); Thomas Marx, Penzberg (DE); Kirsten Sonn, Penzberg (DE); Johann-Peter Thalhofer, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 308 days.

(21) Appl. No.: 12/478,306

(22) Filed: Jun. 4, 2009

(65) Prior Publication Data

US 2010/0086971 A1    Apr. 8, 2010

(30) Foreign Application Priority Data

Jun. 11, 2008 (EP) .................................... 08010580

(51) Int. Cl.
*A61K 35/56* (2006.01)
*A61K 35/12* (2006.01)
*C12N 1/20* (2006.01)
*C12N 9/48* (2006.01)

(52) U.S. Cl. .................... 424/548; 435/243; 435/252.7; 435/212; 424/93.41; 424/247.1; 424/549; 424/520

(58) Field of Classification Search ........................ None
See application file for complete search history.

(56) References Cited

U.S. PATENT DOCUMENTS 6,103,529 A * 8/2000 Price et al. .................... 435/404

FOREIGN PATENT DOCUMENTS

| RU | 2180002 C2 | 2/2002 |
|---|---|---|
| WO | 03/025136 A2 | 3/2003 |
| WO | 2007/089851 A2 | 8/2007 |

OTHER PUBLICATIONS

Aspmo, S.I., Horn, S.J., Eijsink, V.G.H. (2005) Hydrolysates from Atlantic cod (*Gadus morhua* L.) viscera as components of microbial growth media. Process Biochemistry 40: 3714-3722.*

Website document entitled "US Biological—Culture Media" (available at http://www.usbio.net/catalog/Culture%20Media/Media-Ingredients). Downloaded from website Jul. 1, 2011.*
Website document entitled "Media Ingredients, Peptones & Hydrolysates" (available at www.jsunitech.com/product/culture/MediaIngredients.pdf). Downloaded from website Jul. 1, 2011.*
Jayme, D.W. and Smith, S.R. (2000) Media formulation options and manufacturing process controls to safeguard against introduction of animal origin contaminants in animal culture. Cytotechnology 33: 27-36.*
Peterson, J. Sauces: Classical and Contemporary Sauce Making, 3d Ed. John Wiley and Sons, Inc. Hoboken, N.J. 2008, pp. 100-101.*
Website document entitled: "Court Bouillon Recipe" (available at : http://culinaryarts.about.com/od/stocks/r/courtbouillon.htm?p=1). Downloaded from website: Nov. 3, 2011.*
Website document entitled: "How to Poach Fish" (available at : http://culinaryarts.about.com/od/fishseafood/ht/poachfish. htm?p=1). Downloaded from website: Nov. 3, 2011.*
Website document entitled: "Caciucco (fish stew)" (available at : www.italyum.com/index?php?option=com_content&tast=view &id=28&pop=1&page=0&Itemid=33). Downloaded from website: Nov. 3, 2011.*
Website document entitled : " Whole Poached Fish Cold" (available at : http://emeril.com/recipe/5108/Whole-Poached-Fish-Cold). Downloaded from website: Nov. 3, 2011.*
Kocholaty, Walter and Weil, Leopold, "Enzymic Adaptation in *Clostridium histolyticum*," Biochemical Journal, 1938, pp. 1696-1701, vol. 32.
Bond, M. et al., "Characterization of the Individual Collagenases from *Clostridium*," Biochemistry 23 (1984) 3085-3091.
Bond, M. et al., "Purification and Separation of Individual Collagenases of *Clostridium histolyticum* Using Red Dye Ligand Chromatography," Biochemistry 23 (1984) 3077-3085.
Jozwiak, J. et al., "Inhibition of *Clostridium histolyticum* Supernatant Cytotoxic Activity by Protease Inhibitors," Enzyme and Microbial Technology 39 (2006) 28-31.
Kunz, W. et al., "Zur Lehre von der Wirkung der Salze' (about the science of the effect of salts): Franz Hofmeister's historical papers," Current Opinion in Colloid and Interface Science 9 (2004) 13-37.

* cited by examiner

*Primary Examiner* — Chris R Tate
*Assistant Examiner* — Russell Fiebig

(57) ABSTRACT

The present invention provides improved media for the cultivation of *Clostridium histolyticum* and culture supernatants for the biotechnological production of collagenase enzymes. The nutrient media according to the invention comprise one or more peptones from a non-mammalian source, preferably plant-derived peptones. The media can additionally comprise fish gelatin. The invention provides media, culture supernatants comprising *Clostridium histolyticum* collagenase, and methods to produce said collagenase.

12 Claims, No Drawings

GROWTH MEDIUM FOR *CLOSTRIDIUM HISTOLYTICUM*

RELATED APPLICATIONS

This application claims priority to EP 08010580.2 filed Jun. 11, 2008.

FIELD OF THE INVENTION

The present invention is in the field of microbiology. Particularly, the invention deals with the optimization of cultivation media for *Clostridium histolyticum*.

BACKGROUND OF THE INVENTION

The genus *Clostridium* encompasses rod-shaped Gram-positive bacteria which are obligate anaerobes capable of producing endospores. *Clostridium* includes common free-living bacteria as well as important pathogens which include *C. botulinum*, *C. difficile*, *C. perfringens*, *C. tetani*, and *C. histolyticum*. The latter is known for producing collagenases which are exotoxins and act as virulence factors, e.g. by facilitating the spread of gas gangrene. Collagenases normally target the connective tissue in muscle cells and other body organs. Owing to the potent hydrolytic activity toward connective tissue, collagenases and other proteinases such as thermolysin are used for tissue dissociation in vitro.

*C. histolyticum* can be isolated from soil. However, the bacterium is rarely found in wounds. *C. histolyticum* is not strictly anaerobic and can grow weakly on aerobically incubated media. In culture, proteins and peptides are the main carbon source of *C. histolyticum* which secretes a variety of enzymes capable of hydrolyzing peptidic bonds.

For technical applications, collagenases from *C. histolyticum*, i.e. the collagenase of type I and type II, are of particular importance, e.g. for dissociation of organ tissue in vitro. Importantly, collagenase digestion of pancreatic tissue is presently used in the preparation and isolation of human islet cells. However, a number of other different specific cell types have been isolated from attendant connective tissue, including fat cells from adipose tissue, hepatocytes from liver, chondrocytes from cartilage, myocytes from heart, and osteoblasts from bone.

A practical advantage is that *C. histolyticum* can be cultured in large quantities in simple liquid media, and it regularly produces amounts of proteolytic enzymes which are secreted into the culture medium.

RO 51768 discloses a medium for growing *Clostridium histolyticum* in order to produce collagenase, whereby the medium contained peptone and paraffin oil.

RU 2180002 discloses a medium for fermentation and purification of collagenase of *Clostridium histolyticum* comprising casein and soybean oil cake hydrolyzate. Further ingredients were sodium dihydrogen phosphate monohydrate, potassium hydrogen phosphate dihydrate, pyridoxine, riboflavin, thiamine bromide, folic acid, calcium pantothenate, nicotinic acid, lipoic acid, and biotin.

WO 2003/025136 discloses a gelatin-based fermentation medium for the production of cellulose and collagenase from *Clostridium collagenovorans*.

WO 2007/089851 discloses media compositions and processes useful for fermentation of *C. histolyticum*. Proteinaceous constituents of the media included phytone peptone, yeast extract, proteose peptone, tryptone and various vegetable extracts. It was found that a porcine-derived proteose peptone supported the growth of the *C. histolyticum* strains which under these conditions secreted collagenase enzymes into the culture broth. The culture medium with proteose peptone was optimized in order to reduce the content of the co-secreted clostripain protease.

The culture of *C. histolyticum* has historically required the use of animal-derived products such as brain heart infusion (e.g. Jozwiak, J., et al., Enzyme and Microbial Technology 39 (2006) 28-31). However, the requirement of proteinacious material of mammalian origin in the media gives rise to concern over possible contamination of the media. In particular, concern that the media may be contaminated with any transmissible spongiform encephalopathy (TSE) causative agent or other infectious and harmful agents, restricts the usefulness of any factors derived from such cultures, especially in therapeutic applications.

Thus, the cultivation media for *C. histolyticum* of the state of the art have certain disadvantages. In view of this it is an objective of the invention to provide alternative compositions for media to support the growth of *C. histolyticum*. A particular focus of the invention is the provision of growth media free of mammalian-derived ingredients. Furthermore, the invention aims at providing liquid media are useful for fermentation of *C. histolyticum*. Additionally, it is an objective of the invention to provide media which support secretion of enzymes with collagenase activity into the culture medium, and preferably in amounts which allow economic purification of the enzymes from culture supernatant at a large scale.

The inventors have surprisingly found, that the combination of fish gelatin and peptones derived from non-mammalian sources solves the above technical problem.

SUMMARY OF THE INVENTION

A first aspect of the invention is liquid composition for supporting growth of *Clostridium histolyticum* and secretion of collagenase, the composition comprising water, a peptone of non-mammalian source and a fish gelatin. A further aspect of the invention is a sterilized liquid composition according to the invention. Yet, a further aspect of the invention is the use of a composition according to the invention for cultivating *Clostridium histolyticum* and secreting therefrom a protease with collagenase activity. Yet, a further aspect of the invention is a method for producing a supernatant of a *Clostridium histolyticum* liquid culture, the supernatant containing one or more proteases with collagenase activity, the method comprising the steps of (a) providing a sterilized composition according to the invention with an inoculum of *Clostridium histolyticum* bacteria; (b) growing and cultivating (=making a culture, preferably a batch culture, of) the bacteria, whereby the bacteria secrete the one or more proteases with collagenase activity into the liquid phase; (c) separating cellular and other particulate matter from the liquid phase; thereby producing the culture supernatant with one or more proteases with collagenase activity. Yet, a further aspect of the invention is a culture supernatant comprising one or more proteases with collagenase activity from *Clostridium histolyticum*, obtainable by the method of (a) providing a sterilized composition according to the invention with an inoculum of *Clostridium histolyticum* bacteria; (b) growing and cultivating the bacteria, whereby the bacteria secrete the one or more proteases with collagenase activity into the liquid phase; (c) separating cellular and other particulate matter from the liquid phase; thereby obtaining the culture supernatant comprising one or more proteases with collagenase activity from *Clostridium histolyticum*. Yet, a further aspect of the invention is a method for producing one or more purified proteases with collagenase activity from *Clostridium histolyticum*, comprising the steps of (a) providing a sterilized composition according to the invention with an inoculum of *Clostridium histolyticum* bacteria; (b) growing and cultivating the bacteria, whereby the bacteria secrete the one or more proteases with collagenase activity into the liquid phase; (c) separating cellular and other particulate matter from the liquid phase, thereby obtaining a culture supernatant; (d) isolating the one or more proteases with collagenase activity from the culture supernatant; thereby producing the one or more purified proteases with collagenase activity from *Clostridium histolyticum*.

DETAILED DESCRIPTION OF THE INVENTION

Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth below.

The present invention refers to the *C. histolyticum* collagenases (EC 3.4.24.3) of type I and type II as previously given in Bond, M., D., van Wart, H., E., Biochemistry 23 (1984), 3077-3085 and Bond, M., D., van Wart, H., E;. Biochemistry 23 (1984), 3085-3091.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by $n1 \leq x \leq n2$.

If not stated otherwise, it is understood that the term "about" and the character "~" in combination with a numerical value n ("about n", "~n") indicates a value x in the interval given by the numerical value ±5% of the value, i.e. $n-0.05*n \leq x \leq n+0.05*n$. In case the term "about" or the character "~" in combination with a numerical value n describes a preferred embodiment of the invention, the value of n is most preferred, if not indicated otherwise.

Bacterial "growth" is the division of one bacterium into two identical daughter cells during a process called binary fission. Hence, local doubling of the bacterial population occurs. Both daughter cells from the division do not necessarily survive. However, if the number surviving exceeds unity on average, the bacterial population undergoes exponential growth. The measurement of an exponential bacterial growth curve in batch culture can be monitored using well known practice, such as bacterial enumeration (cell counting) by direct and individual (microscopic, flow cytometry), direct and bulk (biomass), indirect and individual (colony counting), or indirect and bulk (most probable number, turbidity, nutrient uptake) methods. Bacterial growth in batch culture can be modeled with four different phases: lag phase (A), exponential or log phase (B), stationary phase (C), and death phase (D).

(A) During "lag phase", bacteria adapt themselves to growth conditions. It is the period where the individual bacteria are maturing and not yet able to divide. (B) "Exponential phase" (sometimes also called the "logarithmic" or "log" phase) is a period characterised by cell doubling. The number of new bacteria appearing per unit time is proportional to the present population. If growth is not limited, doubling will continue at a constant rate so both the number of cells and the rate of population increase doubles with each consecutive time period. The actual rate of growth depends upon the growth conditions, which affect the frequency of cell division events and the probability of both daughter cells surviving. Exponential growth cannot continue indefinitely, however, because the medium is soon depleted of nutrients and enriched with wastes. (C) During "stationary phase", the growth rate slows as a result of nutrient depletion and accumulation of toxic products. This phase is reached as the bacteria begin to exhaust the resources that are available to them. (D) At death phase, bacteria run out of nutrients and die. Spore-forming species undergo sporulation in this phase.

In reality, even in batch culture, the four phases are not well defined. The cells do not reproduce in synchrony without explicit and continual prompting and their logarithmic phase growth is often not ever a constant rate, but instead a slowly decaying rate, a constant stochastic response to pressures both to reproduce and to go dormant in the face of declining nutrient concentrations and increasing waste concentrations.

A "peptone" is understood as being a mixture of any of various water-soluble compounds that form as intermediates during hydrolysis of proteins to amino acids. A peptone is frequently obtained by enzymatic digestion or acid hydrolysis of natural products, such as animal tissues, milk, plants or microbial cultures. There is a large number of available peptones and extracts which can promote and sustain the growth of most organisms. A peptone comprises fragments of proteins and the composition of the fragments depends on the composition of proteins present at the onset of hydrolysis.

Frequently the protein source for the production of a peptone is a waste form arising during the production of meat and diary produce. However, a variety of peptones are available from plant sources. Depending on the source material and any processing thereof (such as purification to a certain degree of the proteinaceous components of the source) before hydrolytic treatment, a number of compounds other than peptides or amino acids can be part of a peptone.

Peptones can for example be derived from animal milk or meat digested by one or more proteolytic enzymes. In addition to containing small peptides, the resulting spray-dried material can include fats, metals, salts, vitamins and many other biological compounds. Another example for a peptone-containing medium is brain heart infusion broth, also referred to herein as "BHI". BHI is a highly nutritious general-purpose growth medium which is particularly useful for fastidious microorganisms It is made by the recuperation of nutrients from boiled cattle hearts and brains. Soluble factors are released into the broth during the boiling procedure. The broth can then be turned into powder for easy distribution.

The term "Gelatin" refers to a solid or semi-solid substance extracted from collagen containing connective tissue of multicellular animals (metazoans). Collagen proteins, herein collectively referred to as "collagen", have a structural function in the extracellular matrix. Collagen proteins are known to occur not only in higher animals such as mammals but even in very primitive sea sponges.

Collagen is the major structural protein found in the skin and bones of all animals. The collagen molecule consists of 3 individual polypeptide chains (alpha chains) which are wound around one another in a triple helix confirmation. This triple helix is stabilized by hydrogen bonds between collagen molecules, which happens as the animal ages. A collagen molecule of three alpha chains would measure 3000 Ångstroms in length (0.3 microns) and 15 Ångstroms in diameter. Each alpha chain has approximately 1050 amino acids connected together. There are twenty different amino acids in each alpha chain, and for each animal type of gelatin, these amino acids are in a specific repeated pattern. Glycine, which represents a third of the amino acids content, is in repeated sequence with two other amino acids. This might be represented as glycine-x-y. It is not unusual for x to be proline and y to be a hydroxyproline residue.

Gelatin is an irreversibly hydrolyzed form of collagen proteins and is produced by partial hydrolysis of collagen extracted from skins, bones, cartilage, connective tissues, organs, and some intestines. The chemical composition of gelatin is similar to that of collagen. Gelatin is formed when the natural molecular bonds between individual collagen strands are broken down into a form that rearranges more easily. Thus, gelatin melts when heated and solidifies when cooled again. Together with water, it forms a semi-solid colloid gel. Depending on its concentration, gelatin can form a solution of high viscosity in water, which sets to a gel on cooling.

Certain forms of gelatin are used as ingredients in the food industry. To this end, large amounts of gelatin are produced from mammalian animals such as cattle, pigs and horses. However, gelatin from alternative sources are known, e.g. fish gelatin. Methods for the extraction of gelatin from fish have been known for some years. In such methods the collagen rich fish skins (particularly of warm water fish species) and to a lesser extent, swim bladders, are treated, to form and extract gelatin. Fish with fins and scales (kosher fish) represent a more palatable source for orthodox Jews, Moslems and many vegetarians.

In nutrient media for growing microorganisms such as bacteria and fungi, peptones and gelatins can serve as an organic source, e.g. for carbon and/or nitrogen.

In the biotech industry a number of technical enzymes for use in pharmaceutical processes are produced in large-scale fermentation processes. An example therefor are *C. histolyticum* collagenase enzymes for the dissociation of organ tissue and the subsequent isolation of target cells from the dissociated organ tissue. Because the microbial culture producing the technical enzymes takes up components from the growth media, it is desirable to develop peptones and extracts free of mammalian pathogenic agents. There is a particular safety-related concern regarding prions and BSE.

For the present invention the authors of this document evaluated peptones from non-mammalian sources as nutrients in a medium for *Clostridium histolyticum*. The aim of this study was to provide a liquid medium which (i) supports growth of the bacteria and (ii) which stimulates secretion of enzymes with collagenase activity into the culture medium. Particularly preferred media stimulated a high volume activity in the culture supernatant. To this end, a number of plant-derived ingredients listed in Table 1a (see Example 3) were used in different concentrations to prepare peptone-based nutrient media listed in Table 2. The plant-derived peptones were compared with BHI as a reference peptone already known to support growth of *C. histolyticum* and secretion of collagenase enzymes. The comparative cultivation experiments are described below in Example 5 and the results with respect to cell density (measured as OD) and collagenase activity in the supernatant are also given in Table 2.

The cultures were grown until the stationary phase was reached. The foregoing parameters were monitored during the growth (exponential) phase of each culture as well as in the stationary phase.

Although it was not very surprising that a peptone-based nutrient medium with 3.7% BHI produced the best results with regards to volume activity, a surprising result was that nutrient media with either 5% VG100 (culture no. 82) or 2.5% SP6, 2.5% VG100 (culture no. 185a) or 1.5% SP6, 1.5% VG100 (culture no. 195) or 5% BP (culture no. 145) produced very similar results, i.e. a volume activity between above 400 U/l and about 495 U/l. Thus, one aspect of the invention is a composition for supporting growth of *C. histolyticum* and secretion of collagenase, the composition comprising water and a peptone nutrient from a plant source selected from the group consisting of (a) VG100 Vegetable peptone No. 1 from pea (VG100) at a concentration of 5% [w/v], (b) Broad bean peptone (BP) at a concentration of 5% [w/v], (c) the combination of VG100 and Soy bean peptone No 110 papainic digest (SP6) at a concentration of 2.5% [w/v] each, and the combination of VG100 and SP6 at a concentration of 1.5% [w/v] each. In a preferred embodiment of the invention the composition is a liquid composition. In a further preferred embodiment of the invention the composition has a pH between about 7.2 and about 7.4 and even more preferred the composition does not comprise further ingredients. Such a composition provides a first basis for economically growing *C. histolyticum* in batch culture and producing enzymes with collagenase activity in the complete absence of animal-derived ingredients.

In order to optimize collagenase volume activity in the culture supernatant further, media were tested in growth experiments whereby combinations of peptone-based nutrients and different gelatins were used. The gelatins are listed in Table 1b (see Example 3). A combination of 3.7% [w/v] BHI and 3% G1 served as a reference.

Very surprisingly, fish gelatin could be shown to enhance collagenase volume activity in the culture supernatant (see Example 6, Table 3). Therefore, another aspect of the invention is the use of fish gelatin in a nutrient medium for growth of *Clostridium histolyticum* and secretion of enzymes with collagenase activity therefrom. A further aspect of the invention is a composition comprising water, a peptone from a non-mammalian source and a fish gelatin. In a preferred embodiment of the invention, the composition is a liquid nutrient medium. It is understood in this regard that in the composition according to the invention the compounds, i.e. the peptone(s) and the gelatin(s) and any other ingredient are dissolved in water, i.e. form a solution. Due to any gelatin ingredient the viscosity of the solution can be higher than pure water.

Fish gelatin differs from conventional gelatins from mammalian sources with respect to its amino acid content. Although all gelatins are composed of the same 20 amino acids, fish gelatin comprises a lower amount of imino acids, proline and hydroxyproline, when compared with gelatins from mammalian sources. In a preferred embodiment of the invention, the hydroxyproline content of the fish gelatin is between about 78% and about 56% compared to calf skin gelatin. In another preferred embodiment of the invention, the proline content of the fish gelatin is between about 93% and about 74% compared to calf skin gelatin.

There are different types of fish gelatin available commercially which can be used in the nutrient media according to the invention. In a very much preferred embodiment of the invention the fish gelatin is selected from the group consisting of (i) high molecular weight fish gelatin, (ii) liquid fish gelatin, (iii)

gelatin from a kosher species of fish, and a mixture thereof. Fish must have fins and scales to be kosher; shellfish, i.e. aquatic invertebrates such as molluscs, crustaceans, echinoderms, and other non-fish water fauna are not kosher. Thus, in a preferred embodiment of the invention gelatin from a kosher species of fish is gelatin from a species of fish (pisces) having fins and scales.

In a very much preferred embodiment of the invention, the concentration of fish gelatin in the composition of the invention is between about 2% and about 10%, whereby the percentage indicates weight by volume when the isolated fish gelatin is dry matter and volume by volume when the isolated fish gelatin is liquid matter. In an even more preferred embodiment of the invention, the concentration of fish gelatin is between about 3% and about 8%.

According to the invention, the peptone in the nutrient composition is a peptone from a non-mammalian source. In a very much preferred embodiment of the invention, the peptone is a plant product. Even more preferred, the peptone is from a plant source selected from the group consisting of soy bean, broad bean, pea, potato, and a mixture thereof. Most preferred, the peptone is selected from the group consisting of Oxoid VG100 Vegetable peptone No. 1 from pea (VG100), Oxoid VG200 Vegetable peptone phosphate broth from Pea (VG200), Merck TSB CASO-Bouillion animal-free (TSB), Invitrogen Soy bean peptone No 110 papainic digest (SP6), Fluka Broad bean peptone (BP), Organotechnie Plant peptone E1 from potato (E1P), and a mixture thereof.

Regarding configuration of the nutrient medium and peptone concentration in particular, it is a very much preferred embodiment of the invention that the composition according to the invention comprises two or more different peptones, whereby the aggregate concentration of the plant peptones in the composition is between about 2% and about 10% weight by volume. Even more preferred, the aggregate concentration of the plant peptones in the composition is between about 3% and about 5% weight by volume.

In another very much preferred embodiment of the invention, a single type of peptone is present in the nutrient composition of the invention, whereby the peptone is selected from the group consisting of BP, E1P, Soy bean peptone E110, VG100, and VG200, and whereby the concentration of the peptone in the composition is about 5% weight by volume. In yet another very much preferred embodiment of the invention, a single type of peptone is present in the nutrient composition of the invention, whereby the peptone is VG100, and whereby the concentration of the peptone in the composition is about 2% weight by volume.

In a preferred embodiment of the invention, the pH of the composition is between pH 7 and pH 8. Even more preferred is a pH between about pH 7.2 and about pH 7.4.

In a further preferred embodiment, the composition according to the invention is sterilized, that is to say the composition is made free of any self-replicating organism. Sterilization can be achieved by standard methods known to the skilled person, e.g. by heat treatment such as autoclaving.

The composition according to the invention is particularly useful for cultivating Clostridium histolyticum bacteria. A most preferred embodiment of the invention is therefore a composition according to the invention additionally comprising an inoculum of Clostridium histolyticum bacteria. Equally preferred in this respect is the use of a composition according to the invention for cultivating Clostridium histolyticum and secreting therefrom a protease with collagenase activity.

Accordingly, another aspect of the invention is a method for producing one or more purified proteases with collagenase activity from Clostridium histolyticum, comprising the steps of (a) providing a sterilized composition according to the invention with an inoculum of Clostridium histolyticum bacteria; (b) growing and cultivating the bacteria, whereby the bacteria secrete the one or more proteases with collagenase activity into the liquid phase; (c) separating cellular and other particulate matter from the liquid phase, thereby obtaining a culture supernatant; (d) purifying the one or more proteases with collagenase activity from the culture supernatant; thereby producing the one or more purified proteases with collagenase activity from Clostridium histolyticum.

Yet, another aspect of the invention is a culture supernatant comprising one or more proteases with collagenase activity from Clostridium histolyticum, obtainable by the method of (a) providing a sterilized composition according to the invention with an inoculum of Clostridium histolyticum bacteria (b) growing and cultivating the bacteria, whereby the bacteria secrete the one or more proteases with collagenase activity into the liquid phase; (c) separating cellular and other particulate matter from the liquid phase; thereby obtaining the culture supernatant comprising one or more proteases with collagenase activity from Clostridium histolyticum. A culture supernatant according to the invention is a complex mixture comprising not only collagenases but also other secreted proteins. In a very much preferred embodiment of the invention the supernatant is obtained from a liquid culture in the stationary phase.

The supernatant according to the invention can be used directly for the purification of one or more ingredient contained therein. Alternatively, the supernatant can be stored, e.g. in frozen form. However, most preferred is storing a lyophilizate of the supernatant. Thus, a further aspect of the invention is a lyophilizate of the supernatant according to the invention.

In yet more detail, the present invention is described by the following items which represent preferred embodiments thereof.

1. A liquid composition comprising water, a peptone from a non-mammalian source and a fish gelatin.

2. The composition according to item 1, characterized in that the fish gelatin is selected from the group consisting of high molecular weight fish gelatin, gelatin from a kosher species of fish, liquid fish gelatin, and a mixture thereof.

3. The composition according to item 2, characterized in that the fish gelatin is selected from the group consisting of high molecular weight fish gelatin, kosher fish gelatin, and a mixture thereof.

4. The composition according to any of the items 1 to 3, characterized in that the concentration of fish gelatin in the composition is between about 2% and about 10%, whereby the percentage indicates weight by volume when the isolated fish gelatin is dry matter and volume by volume when the isolated fish gelatin is liquid matter.

5. The composition according to item 4, characterized in that the concentration of fish gelatin is between about 3% and about 8%.

6. The composition according to any of the items Ito 5, characterized in that the peptone of non-mammalian source is not fish peptone.

7. The composition according to item 6, characterized in that the peptone of non-mammalian source is a plant product.

8. The composition according to item 7, characterized in that the plant source of the peptone is from a plant source selected from the group consisting of soy bean, broad bean, pea, potato, and a mixture thereof.

9. The composition according to item 8, characterized in that the peptone is selected from the group consisting of VG100 Vegetable peptone No. 1 from pea (VG100), VG200 Vegetable peptone phosphate broth from Pea (VG200), TSB CASO-Bouillion animal-free (TSB), Soy bean peptone Not 10 papainic digest (SP6), Broad bean peptone (BP), Plant peptone E1 from potato (E1P), and a mixture thereof.

10. The composition according to item 9, characterized in that the composition comprises two or more different peptones, whereby the aggregate concentration of the plant peptones in the composition is between about 2% and about 10% weight by volume.

11. The composition according to item 10, characterized in that the aggregate concentration of the plant peptones is between about 3% and about 5% weight by volume.

12. The composition according to item 9, characterized in that the peptone is selected from the group consisting of BP, E1P, Soy bean peptone E110, VG100, and VG200, whereby the concentration of the peptone in the composition is about 5% weight by volume.

13. The composition according to item 9, characterized in that the peptone is VG100, whereby the concentration of the peptone in the composition is about 2% weight by volume.

14. The composition according to any of the items 1 to 13, characterized in that the pH of the composition is between pH 7 and pH 8.

15. A sterilized composition according to any of the items 1 to 14.

16. The composition according to item 15, additionally comprising an inoculum of *Clostridium histolyticum* bacteria.

17. Use of a composition according to item 15 or item 16 for cultivating *Clostridium histolyticum* and secreting therefrom a protease with collagenase activity.

18. A method for producing a supernatant of a *Clostridium histolyticum* liquid culture, the supernatant containing one or more proteases with collagenase activity, the method comprising the steps of
  (a) providing a sterilized composition with an inoculum according to item 16;
  (b) growing and cultivating the bacteria, whereby the bacteria secrete the one or more proteases with collagenase activity into the liquid phase;
  (c) separating cellular and other particulate matter from the liquid phase, thereby obtaining a culture supernatant;
  thereby producing a culture supernatant with one or more proteases with collagenase activity.

19. A method for producing one or more purified proteases with collagenase activity from *Clostridium histolyticum*, comprising the steps of
  (a) providing a sterilized composition with an inoculum according to item 16;
  (b) growing and cultivating the bacteria, whereby the bacteria secrete the one or more proteases with collagenase activity into the liquid phase;
  (c) separating cellular and other particulate matter from the liquid phase, thereby obtaining a culture supernatant;
  (d) isolating the one or more proteases with collagenase activity from the culture supernatant;
  thereby producing one or more purified proteases with collagenase activity from *Clostridium histolyticum*.

20. A culture supernatant comprising one or more proteases with collagenase activity from *Clostridium histolyticum*, obtainable by the method of
  (a) providing a sterilized composition with an inoculum according to item 16;
  (b) growing and cultivating the bacteria, whereby the bacteria secrete the one or more proteases with collagenase activity into the liquid phase;
  (c) separating cellular and other particulate matter from the liquid phase;
  thereby obtaining the culture supernatant comprising one or more proteases with collagenase activity from *Clostridium histolyticum*.

The following examples are provided to aid the understanding of the present invention, the true scope of which is set forth in the appended claims. It is understood that modifications can be made in the procedures set forth without departing from the spirit of the invention.

EXAMPLE 1

General Working Conditions

Generally, all working steps involving bacteria or bacterial cultures were performed under sterile conditions applying standard laboratory practice in microbiology. Anaerobic cultures were kept under a nitrogen atmosphere in incubators at a temperature of 30° C. Transfer of inoculum was performed under ambient (i.e. oxygen containing) atmosphere under a laminar flow hood. All media described in this document were sterilized by autoclaving. Adjustments of the pH, in the range of pH 7.2-pH 7.4 if not indicated otherwise, were made before autoclaving. If not indicated otherwise, 1 mM $CaCl_2$ was added per 1 l of any respective medium. Aliquots of autoclaved media were routinely checked for pH changes.

EXAMPLE 2

Seed Culture, Seed Bank and Starter Culture of *C. histolyticum* Bacteria

*Clostridium histolyticum* strain BMTU 1175 which is a derivative of ATCC 21000 was used as inoculum of a volume of 100 ml of liquid growth medium consisting of 3.7% of BHI and 3.0% of G1 dissolved in water with a pH adjusted at pH 7.2. The culture was incubated for about 26 h under anaerobic conditions until an optical density at 578 nm ($=OD_{578nm}$) of 5.6 was reached. Aliquots of 1 ml of this liquid culture were sealed in ampullae, frozen and stored in the gas phase of liquid nitrogen. The aliquots served as the primary seed bank for further use as starter cultures.

Starter cultures for growth experiments in different media were prepared by inoculating 100 ml of a liquid medium containing 5% [w/v] VG100 with the contents of a 1 ml seed bank ampulla, and incubating the bacteria unter anaerobic conditions at 30° C. overnight or at 37° C. for about 8 h. Liquid media (at a volume of usually 100 ml or 200 ml) as described further below were each inoculated with between about 2-4 ml of starter culture.

EXAMPLE 3

Culture of *C. histolyticum* in Different Media

Growth of *C. histolyticum* in different growth media was assessed. Liquid cultures were incubated in flasks without agitation. If not indicated otherwise, incubations of the cultures lasted 40 h. During each experiment at different time points one or more samples were drawn from the culture and the $OD_{578nm}$ of the liquid culture, the pH of the culture supernatant and collagenase proteolytic activity in the culture supernatant (see Example 4) were assayed.

Liquid media were prepared using the ingredients listed in Tables 1a and 1b. If not indicated otherwise, concentrations of ingredients given as percentage indicate % weight by volume [w/v], adjusted before autoclaving. For example, a concentration of 3% [w/v] of a given compound corresponds to 3 g/100 ml of medium. In the case of G4 which is a liquid ingredient, the concentration given as percentage indicates % volume by volume.

Adjustments of the pH, in the range of pH 7.2-pH 7.4 if not indicated otherwise, were made before autoclaving. If not indicated otherwise, 1 mM $CaCl_2$ was added per 1 l of any respective medium.

TABLE 1a

Commercially available peptone compounds tested in growth media

| Abbreviation | Compound | Source | Provider, product designation or catalog no. |
|---|---|---|---|
| A2SC | Soy peptone A2 SC | Soy bean | Organotechnie, 19649 |
| A3SC | Soy peptone A3 SC | Soy bean | Organotechnie, 19685 |
| A482 | Pea peptone A482 | Pea | Organotechnie, AI275 |
| AM41 | Soy peptone AM41 | Soy bean | Organotechnie, AI230 |
| BHI | Brain heart infusion | Bovine | BD (Difco), 0037-8 |
| BP | Broad bean peptone | Broad bean | Fluka, 93491 |
| E1 | Wheat peptone E1 | Wheat | Organotechnie, 19559 |
| E110 | Soy bean peptone E110 | Soy bean | Organotechnie, AI885 |
| E1P | Plant peptone E1 | Potato | Organotechnie, 19025 |
| E430 | Wheat peptone E430 | Wheat | Organotechnie, AI233 |
| ET1 | Plant peptone ET1 | Potato | Organotechnie, 19725 |
| YE | Yeast Extract | Yeast 1 | BD (Difco), 886-08-1 |
| L85 | Proteose peptone | Mammalian source | Oxoid, LP0085 |
| SP4 | Soy bean peptone | Soy bean | Biofac Denmark, 21 |
| SP5 | Peptone from soy bean meal (papainic digest) | Soy bean | Merck, 7212 |
| SP6 | Soy bean peptone No110 (papainic digest) | Soy bean | Invitrogen, 152-90059 |
| SP7 | Hy Pep 1510 | Soy bean | Kerry, 1510 |
| SP8 | HyPep 5603 | Soy bean | Kerry, 5603 |
| T | Tryptone Bacto | Milk (bovine) | BD (Difco), 123-08-4 |
| TSB | TSB (CASO-Bouillion, animal free) | Plant | Merck, 525 |
| VG100 | Vegetable peptone No 1 | Pea | Oxoid, VG0100 |
| VG101 | Vegetable peptone broth | Pea | Oxoid, VG0101 |
| VG200 | Vegetable peptone phosphate broth | Pea | Oxoid, VG0200 |
| VG300 | Veggietone soy peptone | Soy bean | Oxoid, VG0300 |

TABLE 1b

Commercially available gelatin compounds tested in growth media

| Abbreviation | Compound | Source | Provider, product designation or catalog no. |
|---|---|---|---|
| G1 | Gelita-Sol D | Porcine/bovine | DGF Stoess, Gelita-Sol D |
| G2 | High molecular weight dried fish gelatin | Fish | Kenney&Ross, HMWD |
| G3 | Kosher dried fish gelatin | Fish | Kenney&Ross, KD |
| G4 | Liquid fish gelatin | Fish | Kenney&Ross, HIPURE LIQUID GELATIN (Technical Gelatin) |
| G2T | Tryptic digest of G2 | Fish | G2 was dissolved in water; before sterilization trypsin‡ was added to a final concentration of 70 mg/ml; the mixture was incubated for 1 h at 37° C. and autoclaved afterwards. |
| G3T | Tryptic digest of G3 | Fish | G3 was dissolved in water; before sterilization trypsin‡ was added to a final concentration of 70 mg/ml; the mixture was incubated for 1 h at 37° C. and autoclaved afterwards. |

‡recombinantly produced trypsin from Roche Applied Science (Roche Diagnostics GmbH, Mannheim, Germany).

EXAMPLE 4

Assay to Determine Collagenase Proteolytic Activity

Collagenase proteolytic activity was measured by a standard method in Wuensch units (Wuensch, E., Heidrich, H., Z., Physiol. Chem. 333 (1963) 149-159) using a synthetic peptide substrate. Collagenase protcolytic activity catalyses the hydrolysis of the modified substrate ("Wuensch") peptide 4-phenylazo-benzyloxycarbonyl-Pro-Leu-Gly-Pro-Arg (Bachem M1715) between the Leu and the Gly residue. One unit (U) of activity is defined by the hydrolysis of 1 μM peptide per minute at 25° C., pH 7.1.

The substrate peptide (also referred to as "substrate") was provided in a solution and at a concentration of 1 mg/ml. 10 mg substrate peptide were first dissolved in 0.2 ml methanol. The volume of the solution was increased to 10 ml by adding 0.1 M TrisHCl, pH 7.1. Further reagents were a 0.1 M $CaCl_2$ solution in water and an extraction mixture consisting of 5 volume parts ethyl acetate and 1 volume part 0.025 M citric acid in water. Drying tubes were provided as test tubes containing 0.35-0.4 g $(NH_4)_2SO_4$. Before use each drying tube was sealed with parafilm.

Control and sample reactions were set up in test tubes according to the following pipetting scheme and workflow:

| Step | Solution | Control test tube | Sample test tube |
|---|---|---|---|
| 1 | Substrate peptide | 1 ml | 1 ml |
|   | CaCl$_2$ | 0.2 ml | 0.2 ml |
|   | Mix, warm to 25° C. | | |
| 2 | Sample material[§] | — | 0.05 ml |
|   | 0.1 M TrisHCl, pH 7.1 | 0.05 ml | — |
| | Mix, incubate for 15 min at 25° C.; after incubation an aliquot of the incubated solution is transferred to a volume of the extraction mixture | | |
| 3 | Incubated solution of step 2 | 0.5 ml | 0.5 ml |
|   | Extraction mixture | 6 ml | 6 ml |
| | Mix immediately by vortexing for 20 s, transfer about 3 ml of ethyl acetate phase into a drying tube, mix by vortexing and transfer supernatant into cuvette; measure extinction (A) at 320 nm, cuvette light path = 1 cm. | | |
| 4 | Calculate volume activity | | |
|   | [U/ml] = ΔA * d * 0.794 | | |

A: measured extinction value
d: dilution factor
ΔA = A$_{sample}$ − A$_{control}$
[§] a solution comprising one or more enzymes with collagenase proteolytic activity. If necessary, sample material used in the assay was prepared by diluting the solution. For each measurement the respective dilution factor (d) was adjusted and chosen in order to finally result in an extinction value between 0.3 and 1.0. However, usually undiluted culture supernatant cleared from bacterial cells and debris was assayed. Additionally, standards with known amounts of collagenase and known activity were tested as references.

In mixtures containing both collagenase type I and type II enzymes the measured activity of collagenase II is usually greater than the activity of collagenase I, when performing activity assays using the Wuensch peptide as a substrate. Thus, under the conditions applied any measured proteolytic activity mainly reflects collagenase type II.

EXAMPLE 5

Growth of *C. histolyticum* in Different Media: Peptone-Based Media without Addition of Gelatin Table 2 provides a number of media for the cultivation of *C. histolyticum*. Each table entry shows the ingredients of the respective medium. In some cases the pH that was adjusted before sterilization of the medium and inoculation. In case no pH value is tabulated, the medium was inoculated following pH adjustment with KOH to a value of between pH 7.2 and pH 7.4, if not indicated otherwise. Cultures were grown into the stationary phase corresponding to an incubation for about 40 h under standard conditions. The optical density at 578 nm (also referred to as "OD") was determined when the culture was terminated, as well as the collagenase enzymatic activity in the culture supernatant (see Example 4). In the table volume activity is given in Wuensch units per liter of medium (also referred to as "U/l" in the tabulated data).

TABLE 2

Composition and pH of liquid media before inoculation, growth yield of *C. histolyticum* and collagenase activity in the culture supernatant; media are ranked according to collagenase volume activity

| Rank | Culture no. | Composition (peptones) | pH (at 0 h) | OD (~40 h) | Collagenase activity in [U/l] |
|---|---|---|---|---|---|
| 1 | 98 | 3.7% BHI | | 1.7 | 494 |
| 2 | 9 | 3.7% BHI | 7.4 | 1.2 | 493 |
| 3 | 17 | 3.7% BHI | 7.4 | 1.3 | 460 |
| 4 | 82 | 5% VG100 | | 1.9 | 451 |
| 5 | 185a | 2.5% SP6 | | 1.6 | 446 |
| | | 2.5% VG100 | | | |
| 6 | 195 | 1.5% SP6 | | 0.6 | 443 |
| | | 1.5% VG100 | | | |
| 7 | 145 | 5% BP | | 1.7 | 428 |

TABLE 2-continued

Composition and pH of liquid media before inoculation, growth yield of *C. histolyticum* and collagenase activity in the culture supernatant; media are ranked according to collagenase volume activity

| Rank | Culture no. | Composition (peptones) | pH (at 0 h) | OD (~40 h) | Collagenase activity in [U/l] |
|---|---|---|---|---|---|
| 8 | 175 | 2.5% SP6 (Lot "B") | 7.4 | 1.6 | 409 |
| | | 2.5% VG100 | | | |
| 9 | 185b | 2.5% SP6 | | 1.9 | 403 |
| | | 2.5% VG100 | | | |
| 10 | 94 | 2.5% VG100 | | 1.7 | 401 |
| | | 2.5% TSB | | | |
| 11 | 171 | 1.25% SP6 (Lot "B") | 7.4 | 1.5 | 374 |
| | | 1.25% VG100 | | | |
| | | 1.25% TSB | | | |
| | | 1.25% BP | | | |
| 12 | 90 | 5% VG100 | | 3.5 | 341 |
| | | 5% TSB | | | |
| 13 | 184 | 6% VG100 | 7.5 | 2.0 | 323 |
| 14 | 78 | 5% SP6 | | 1.9 | 308 |
| 15 | 177 | 2.5% SP6 (Lot "B") | 7.3 | 1.4 | 307 |
| | | 512.5% TSB | | | |
| 16 | 173 | 2.5% TSB | 7.4 | 1.5 | 301 |
| | | 2.5% BP | | | |
| 17 | 135 | 5% E1P | 7.4 | 2.3 | 294 |
| 18 | 167 | 5% SP6 (Lot "B") | 7.3 | 1.5 | 290 |
| 19 | 159 | 2.5% VG100 | | 1.7 | 289 |
| | | 2.5% BP | | | |
| 20 | 72 | 5% TSB | 7.3 | 1.1 | 281 |
| 21 | 28 | 5% SP6 | 7.3 | 2.3 | 279 |
| 22 | 165 | 5% SP6 (Lot "A") | 7.4 | 1.5 | 275 |
| 24 | 153 | 1.7% BP | | 2.0 | 268 |
| | | 1.7% TSB | | | |
| | | 1.7% VG100 | | | |
| 25 | 169 | 5% SP6 (Lot "C") | 7.3 | 1.6 | 260 |
| 26 | 183 | 4% VG100 | 7.5 | 1.3 | 258 |
| 27 | 179 | 2.5% SP6 (Lot "B") | 7.4 | 1.6 | 248 |
| | | 2.5% BP | | | |
| 28 | 25 | 4% SP6 | 7.3 | 1.7 | 218 |
| 29 | 71 | 5% SP6 | 7.3 | 3.1 | 218 |
| | | 3% T | | | |
| 30 | 181 | 2% VG100 | 7.5 | 0.4 | 197 |
| 31 | 143 | 2.5% VG200 | 7.4 | 1.5 | 186 |
| | | 2.5% BP | | | |
| 32 | 74 | 5% VG100 | 7.3 | 2.0 | 177 |
| 33 | 161 | 2.5% VG101 | | 2.1 | 177 |
| | | 2.5% BP | | | |
| 34 | 133 | 5% E110 | 7.3 | 1.6 | 166 |
| 35 | 21 | 3% SP6 | 7.3 | 1.0 | 160 |
| 36 | 125 | 5% A482 | 7.3 | 2.6 | 160 |
| 37 | 149 | 5% BP | | 2.0 | 159 |
| 38 | 155 | 1% BP | | 1.0 | 159 |
| | | 1% TSB | | | |
| | | 1% VG100 | | | |
| 39 | 69 | 5% SP6 | 7.3 | 3.2 | 142 |
| | | 3% YE | | | |
| 40 | 139 | 5% ET1 | 7.3 | 13.0 | 137 |
| 41 | 70 | 5% SP6 | 7.3 | 2.0 | 134 |
| | | 1% T | | | |
| 42 | 15 | 2% SP7 | 7.3 | 0.3 | 131 |
| 43 | 14 | 2% SP6 | 7.3 | 0.6 | 130 |
| 44 | 68 | 5% SP6 | 7.3 | 2.2 | 120 |
| | | 1% YE | | | |
| 45 | 157 | 2.5% VG200 | | 1.7 | 119 |
| | | 2.5% TSB | | | |
| 46 | 66 | 5% SP6 | 7.3 | 1.7 | 110 |
| 47 | 106 | 5% VG300 | | 1.6 | 107 |
| 48 | 19 | 3% SP4 | 7.3 | 0.8 | 105 |
| 49 | 26 | 5% SP4 | 7.3 | 1.5 | 104 |
| 50 | 163 | 2.5% VG101 | | 2.2 | 94 |
| | | 2.5% TSB | | | |
| 51 | 13 | 2% SP5 | 7.3 | 0.3 | 92 |
| 52 | 29 | 5% SP7 | 7.3 | 1.9 | 92 |
| 53 | 65 | 5% SP6 | 7.3 | 1.8 | 87 |
| 54 | 129 | 5% AM41 | 7.4 | 1.6 | 79 |
| 55 | 121 | 5% VG200 | | 1.8 | 64 |
| 56 | 137 | 5% A2SC | 7.4 | 1.5 | 62 |

TABLE 2-continued

Composition and pH of liquid media before inoculation, growth yield of *C. histolyticum* and collagenase activity in the culture supernatant; media are ranked according to collagenase volume activity

| Rank | Culture no. | Composition (peptones) | pH (at 0 h) | OD (~40 h) | Collagenase activity in [U/l] |
|---|---|---|---|---|---|
| 57 | 110 | 5% BP | | 1.4 | 60 |
| 58 | 141 | 5% A3SC | 7.3 | 1.5 | 60 |
| 59 | 102 | 5% VG101 | | 1.9 | 46 |
| 60 | 86 | 5% TSB | | 1.0 | 28 |
| 61 | 127 | 5% E430 | 7.4 | 1.4 | 16 |
| 62 | 131 | 5% E1 | 7.4 | 1.2 | 9 |

It was noted that among the media containing peptones only (i.e. without any gelatin added) BHI was most efficient in stimulating secretion of *C. histolyticum* collagenase into the culture supernatant. It was also found that volume activity of collagenase was not merely a function of the OD of the culture.

EXAMPLE 6

Growth of *C. histolyticum* in Different Media: Peptone-Based Media with Gelatin Different types of gelatin from different sources were added to peptone media. Table 3 provides a number of media for the cultivation of *C. histolyticum*. Each table entry shows the ingredients of the respective medium. In some cases the pH that was adjusted before sterilization of the medium and inoculation. In case no pH value is tabulated, the medium was inoculated following pH adjustment with KOH to a value of between pH 7.2 and pH 7.4, if not indicated otherwise. Cultures were grown into the stationary phase corresponding to an incubation for about 40 h under standard conditions. The optical density at 578 nm (also referred to as "OD") was determined when the culture was terminated, as well as the collagenase enzymatic activity in the culture supernatant (see Example 4). In the table volume activity is given in Wuensch units per liter of medium (also referred to as "U/l" in the tabulated data).

TABLE 3

| Composition and pH of liquid media before inoculation, growth yield of *C. histolyticum* and collagenase activity in the culture supernatant; media are ranked according to collagenase volume activity | | | | | | |
|---|---|---|---|---|---|---|
| Rank | Cult. No. | Composition (peptones) | Composition (gelatins) | pH (at 0 h) | OD (~40 h) | Collagenase activity in [U/l] |
| 1 | 199 | 1.5% SP6<br>1.5% VG100 | 5% G2 | | 5.5 | 1405 |
| 2 | 198 | 1.5% SP6<br>1.5% VG100 | 4% G2 | | 5.0 | 1064 |
| 3 | 190 | 2.5% SP6<br>2.5% VG100 | 10% G2 | | 9.8 | 980 |
| 4 | 218 | 1% VG100<br>1% SP6<br>1% TSB<br>1% BP<br>1% E1P | 6% G3 | | 9.6 | 965 |
| 5 | 113 | 5% BP | 3% G3 | | 5.7 | 944 |
| 6 | 197 | 1.5% SP6<br>1.5% VG100 | 3% G2 | | 2.8 | 944 |
| 7 | 220 | 0.6% VG100<br>0.6% SP6<br>0.6% TSB<br>0.6% BP<br>0.6% E1P | 6% G3 | | 8.1 | 933 |
| 8 | 207 | 1% VG100<br>1% SP6<br>1% TSB | 6% G3 | | 8.8 | 928 |
| 9 | 203 | 1.5% SP6<br>1.5% VG100 | 5% G3 | | 6.0 | 920 |
| 10 | 204 | 1.5% SP6<br>1.5% VG100 | 10% G3 | | 11.5 | 913 |
| 11 | 221 | 0.4% VG100<br>0.4% SP6<br>0.4% TSB<br>0.4% BP<br>0.4% E1P | 4% G3 | | 4.6 | 905 |
| 12 | 215 | 1% VG100<br>1% SP6<br>1% E1P | 6% G3 | | 8.0 | 886 |
| 13 | 212 | 1% VG100<br>1% SP6<br>1% BP | 8% G3 | | 14.0 | 885 |
| 14 | 217 | 1% VG100<br>1% SP6<br>1% TSB<br>1% BP<br>1% E1P | 4% G3 | | 6.5 | 885 |
| 15 | 151 | 5% BP | 3% G2 | § | 5.6 | 870 |

TABLE 3-continued Composition and pH of liquid media before inoculation, growth yield of *C. histolyticum* and collagenase activity in the culture supernatant; media are ranked according to collagenase volume activity

| Rank | Cult. No. | Composition (peptones) | Composition (gelatins) | pH (at 0 h) | OD (~40 h) | Collagenase activity in [U/l] |
|---|---|---|---|---|---|---|
| 16 | 208 | 1% VG100<br>1% SP6<br>1% TSB | 8% G3 | | 11.9 | 863 |
| 17 | 147 | 5% BP | 3% G2 | $ | 5.5 | 861 |
| 18 | 174 | 2.5% TSB<br>2.5% BP | 3% G2 | 7.4 | 4.6 | 861 |
| 19 | 112 | 5% BP | 3% G2 | | 5.0 | 857 |
| 20 | 216 | 1% VG100<br>1% SP6<br>1% E1P | 8% G3 | | 12.0 | 856 |
| 21 | 189 | 2.5% SP6<br>2.5% VG100 | 5% G2 | | 7.0 | 856 |
| 22 | 222 | 0.4% VG100<br>0.4% SP6<br>0.4% TSB<br>0.4% BP<br>0.4% E1P | 6% G3 | | 7.3 | 834 |
| 23 | 214 | 1% VG100<br>1% SP6<br>1% E1P | 4% G3 | | 6.0 | 830 |
| 24 | 228 | 1% VG100<br>1% SP6<br>1% BP | 6% G3 | | 8.7 | 809 |
| 25 | 211 | 1% VG100<br>1% SP6<br>1% BP | 6% G3 | | 8.7 | 806 |
| 26 | 196 | 1.5% SP6<br>1.5% VG100 | 2% G2 | | 2.2 | 804 |
| 27 | 148 | 5% BP | 3% G3 | $ | 5.5 | 798 |
| 28 | 219 | 0.6% VG100<br>0.6% SP6<br>0.6% TSB<br>0.6% BP<br>0.6% E1P | 4% G3 | | 5.2 | 792 |
| 29 | 231 | 1% VG100<br>1% SP6<br>1% BP | 8% G3 | | 13.2 | 790 |
| 30 | 233 | 1% VG100<br>1% SP6<br>1% BP | 8% G3 | | 13.4 | 785 |
| 31 | 223 | 1% TSB<br>1% BP<br>1% E1P | 4% G3 | | 5.2 | 756 |
| 32 | 229 | 1% VG100<br>1% SP6<br>1% BP | 6% G3 | | 8.9 | 740 |
| 33 | 202 | 1.5% SP6<br>1.5% VG100 | 4% G3 | | 5.9 | 726 |
| 34 | 224 | 1% TSB<br>1% BP<br>1% E1P | 6% G3 | | 6.7 | 719 |
| 35 | 188 | 2.5% SP6<br>2.5% VG100 | 4% G2 | | 6.8 | 699 |
| 36 | 136 | 5% E1P | 3% G2 | 7.4 | 6.1 | 697 |
| 37 | 230 | 1% VG100<br>1% SP6<br>1% BP | 6% G3 | | 9.0 | 693 |
| 38 | 152 | 5% BP | 3% G3 | § | 6.4 | 693 |
| 39 | 232 | 1% VG100<br>1% SP6<br>1% BP | 8% G3 | | 14.0 | 692 |
| 40 | 96 | 2.5% VG100<br>2.5% TSB | 3% G2 | | 4.6 | 690 |
| 41 | 182 | 2% VG100 | 3% G2 | 7.4 | 3.0 | 687 |
| 42 | 194 | 2.5% SP6<br>2.5% VG100 | 5% G3 | | 8.4 | 685 |
| 43 | 201 | 1.5% SP6<br>1.5% VG100 | 3% G3 | | 3.6 | 682 |
| 44 | 210 | 1% VG100<br>1% SP6<br>1% BP | 4% G3 | | 6.6 | 662 |

TABLE 3-continued

Composition and pH of liquid media before inoculation, growth yield of C. histolyticum and collagenase activity in the culture supernatant; media are ranked according to collagenase volume activity

| Rank | Cult. No. | Composition (peptones) | Composition (gelatins) | pH (at 0 h) | OD (~40 h) | Collagenase activity in [U/l] |
|---|---|---|---|---|---|---|
| 45 | 154 | 1.7% BP<br>1.7% TSB<br>1.7% VG100 | 3% G3 | | 5.7 | 662 |
| 46 | 225 | 1% VG100<br>1% SP6<br>1% BP | 4% G3 | | 6.5 | 643 |
| 47 | 193 | 2.5% SP6<br>2.5% VG100 | 4% G3 | | 6.8 | 637 |
| 48 | 92 | 5% VG100<br>5% TSB | 3% G2 | | 6.4 | 635 |
| 49 | 226 | 1% VG100<br>1% SP6<br>1% BP | 4% G3 | | 5.9 | 627 |
| 50 | 213 | 1% VG100<br>1% SP6<br>1% E1P | 2% G3 | | 2.7 | 618 |
| 51 | 123 | 5% VG200 | 3% G2 | | 6.2 | 611 |
| 52 | 186 | 2.5% SP6<br>2.5% VG100 | 2% G2 | | 3.8 | 608 |
| 53 | 227 | 1% VG100<br>1% SP6<br>1% BP | 4% G3 | | 6.4 | 604 |
| 54 | 323 | 1.5% VG100<br>0.75% SP6<br>0.75% TSB | 7.5% G4 | 7.7 | | 600 |
| 55 | 93 | 5% VG100<br>5% TSB | 3% G3 | | 6.9 | 600 |
| 56 | 187 | 2.5% SP6<br>2.5% VG100 | 3% G2 | | 5.2 | 598 |
| 57 | 321 | 1.5% VG100<br>0.75% SP6<br>0.75% TSB | 7.5% G4 | 7.7 | | 589 |
| 58 | 317 | 1.5% VG100<br>0.75% SP6<br>0.75% TSB | 5.5% G4 | 7.7 | | 589 |
| 59 | 205 | 1% VG100<br>1% SP6<br>1% TSB | 2% G3 | | 3.3 | 579 |
| 60 | 322 | 1.5% VG100<br>0.75% SP6<br>0.75% TSB | 7.5% G4 | 7.7 | | 578 |
| 61 | 318 | 1.5% VG100<br>0.75% SP6<br>0.75% TSB | 5.5% G4 | 7.7 | 2.6 | 577 |
| 62 | 319 | 1.5% VG100<br>0.75% SP6<br>0.75% TSB | 5.5% G4 | 7.7 | | 571 |
| 63 | 100 | 3.7% BHI | 3% G2 | | 5.8 | 563 |
| 64 | 77 | 3.7% BHI | 3% G1 | 7.3 | 3.0 | 562 |
| 65 | 209 | 1% VG100<br>1% SP6<br>1% BP | 2% G3 | | 3.3 | 559 |
| 66 | 320 | 1.5% VG100<br>0.75% SP6<br>0.75% TSB | 5.5% G4 | 7.7 | | 555 |
| 67 | 313 | 1.5% VG100<br>0.75% SP6<br>0.75% TSB | 4% G4 | 7.7 | | 549 |
| 69 | 144 | 2.5% VG200<br>2.5% BP | 3% G2 | 7.4 | 5.7 | 549 |
| 70 | 324 | 1.5% VG100<br>0.75% SP6<br>0.75% TSB | 7.5% G4 | 7.7 | 3 | 540 |
| 71 | 97 | 2.5% VG100<br>2.5% TSB | 3% G3 | | 5.0 | 538 |
| 72 | 314 | 1.5% VG100<br>0.75% SP6<br>0.75% TSB | 4% G4 | 7.7 | | 536 |
| 73 | 242 | 1% VG100<br>1% SP6<br>1% BP | 8% G3T | | 13.7 | 535 |

TABLE 3-continued

Composition and pH of liquid media before inoculation, growth yield of C. histolyticum and collagenase activity in the culture supernatant; media are ranked according to collagenase volume activity

| Rank | Cult. No. | Composition (peptones) | Composition (gelatins) | pH (at 0 h) | OD (~40 h) | Collagenase activity in [U/l] |
|---|---|---|---|---|---|---|
| 74 | 156 | 1% BP<br>1% TSB<br>1% VG100 | 3% G3 | | 4.2 | 527 |
| 75 | 160 | 2.5% VG100<br>2.5% BP | 3% G3 | | 5.0 | 516 |
| 76 | 80 | 5% SP6 | 3% G2 | | 4.3 | 516 |
| 77 | 84 | 5% VG100 | 3% G2 | | 4.5 | 515 |
| 78 | 191 | 2.5% SP6<br>2.5% VG100 | 2% G3 | | 3.9 | 512 |
| 79 | 79 | 5% SP6 | 3% G1 | | 4.5 | 511 |
| 80 | 240 | 1% VG100<br>1% SP6<br>1% BP | 8% G3T | | 13.4 | 509 |
| 81 | 238 | 1% VG100<br>1% SP6<br>1% BP | 6% G3T | | 8.6 | 504 |
| 82 | 235 | 1% VG100<br>1% SP6<br>1% BP | 4% G3T | | 6.2 | 501 |
| 83 | 315 | 1.5% VG100<br>0.75% SP6<br>0.75% TSB | 4% G4 | 7.7 | 1.8 | 500 |
| 84 | 101 | 3.7% BHI | 3% G3 | | 6.6 | 498 |
| 85 | 192 | 2.5% SP6<br>2.5% VG100 | 3% G3 | | 5.9 | 487 |
| 86 | 316 | 1.5% VG100<br>0.75% SP6<br>0.75% TSB | 4% G4 | 7.7 | | 476 |
| 87 | 134 | 5% E110 | 3% G2 | 7.3 | 5.8 | 467 |
| 88 | 241 | 1% VG100<br>1% SP6<br>1% BP | 8% G3T | | 13.2 | 459 |
| 89 | 239 | 1% VG100<br>1% SP6<br>1% BP | 6% G3T | | 8.8 | 459 |
| 90 | 99 | 3.7% BHI | 3% G1 | | 5.6 | 456 |
| 91 | 124 | 5% VG200 | 3% G3 | | 6.1 | 454 |
| 92 | 126 | 5% A482 | 3% G2 | 7.4 | 6.0 | 451 |

§pH adjusted with NH₄OH
$pH adjusted with KOH

It was noted that regarding collagenase volume activity compositions with certain plant peptones in combination with fish gelatin were at least equal and mostly superior to the standard medium containing 3.7% BHI and 3% G1 which are both from mammalian sources. Thus, a multitude of new media is provided for growing and culturing *C. histolyticum* and producing collagenase protease(s) from the supernatants of such cultures.

What is claimed is:

1. A liquid growth medium comprising water, a fish gelatin, a peptone from a non-mammalian source, whereby fish peptone is excluded from the non-mammalian source, wherein the fish gelatin is produced by partial hydrolysis of collagen extracted from skins, bones, cartilage, connective tissues, organs and intestines, wherein the concentration of fish gelatin in the growth medium is between about 2% and about 10%, whereby the percentage indicates weight by volume when the isolated fish gelatin is dry matter and volume by volume when the isolated fish gelatin is liquid matter, and additionally comprising an inoculum of bacteria of the genus *Clostridium.*

2. The growth medium of claim 1 wherein the fish gelatin is selected from the group consisting of high molecular weight fish gelatin, gelatin from a kosher species of fish, and liquid fish gelatin.

3. The growth medium of claim 1 wherein the peptone of non-mammalian source is a plant product.

4. The growth medium of claim 3 wherein the plant product is from selected from the group consisting of soy bean, broad bean, pea, and potato.

5. The growth medium of claim 4 wherein the growth medium comprises two or more different plant peptones, whereby the aggregate concentration of the plant peptones in the growth medium is between about 2% and about 10% weight by volume.

6. The growth medium of claim 1 wherein the peptone is selected from the group consisting of broad bean peptone (BP), peptone E1 from potato (E1P), soy bean peptone E110, vegetable peptone no. 1 from pea (VG100), and vegetable peptone phosphate broth from pea (VG200), and wherein the concentration of the peptone in the growth medium is about 5% weight by volume.

7. The growth medium of claim 1 wherein the peptone is VG100 and the concentration of the peptone in the growth medium is about 2% weight by volume.

8. The growth medium of claim 1 wherein the pH is between 7 and 8.

9. The growth medium of claim 1 wherein the growth medium is sterilized prior to adding the inoculum.

10. The growth medium of claim 9 wherein the inoculum is of *Clostridium histolyticum* bacteria.

11. A method for producing a supernatant of a *Clostridium histolyticum* liquid culture, the supernatant containing one or more proteases with collagenase activity, the method comprising the steps of providing the growth medium according to claim 10, growing and cultivating the inoculum of *Clostridium histolyticum* bacteria, whereby the bacteria secrete the one or more proteases with collagenase activity into the liquid culture, and separating cellular and other particulate matter from the liquid culture, thereby obtaining a culture supernatant with one or more proteases with collagenase activity.

12. A method for producing one or more purified proteases with collagenase activity from *Clostridium histolyticum*, comprising the steps of providing the growth medium according to claim 10, growing and cultivating the inoculum of *Clostridium histolyticum* bacteria, whereby the bacteria secrete the one or more proteases with collagenase activity into the liquid culture, separating cellular and other particulate matter from the liquid culture, thereby obtaining a culture supernatant, and isolating the one or more proteases with collagenase activity from the culture supernatant, thereby producing the one or more purified proteases with collagenase activity from *Clostridium histolyticum*.

* * * * *